United States Patent [19]

Kennedy, Jr.

[11] Patent Number: 5,180,386

[45] Date of Patent: Jan. 19, 1993

[54] METHOD AND DEVICE FOR MAINTAINING OR RESTORING NORMAL LUMBAR CURVATURE

[75] Inventor: Gerald R. Kennedy, Jr., Alma Center, Wis.

[73] Assignee: GraviTech, Inc., Alma Center, Wis.

[21] Appl. No.: 695,691

[22] Filed: May 3, 1991

[51] Int. Cl.$^5$ ............................................. A61F 5/02
[52] U.S. Cl. ................................... 606/240; 128/845; 5/652
[58] Field of Search .................... 128/68, 69, 78, 845, 128/70–74; 5/431, 432, 436, 652; 269/322, 328; 606/237, 240, 241

[56] References Cited

U.S. PATENT DOCUMENTS

| | | |
|---|---|---|
| 1,549,601 | 8/1925 | Mulgrew . |
| 1,667,626 | 3/1927 | Epstein . |
| 3,359,577 | 5/1966 | Rogers . |
| 3,771,518 | 11/1973 | Greissing . |
| 3,974,827 | 8/1976 | Bodeen . |
| 4,126,129 | 11/1978 | Rainbow . |
| 4,350,152 | 9/1982 | Strakowski . |
| 4,474,370 | 10/1984 | Oman . |
| 4,475,543 | 10/1984 | Brooks et al. . |
| 4,502,170 | 3/1985 | Morrow ................................. 5/632 |
| 4,597,386 | 7/1986 | Goldstein . |
| 4,669,455 | 6/1987 | Bellati . |
| 4,796,315 | 1/1989 | Crew . |
| 4,903,412 | 2/1990 | Pedrow . |
| 4,905,993 | 3/1990 | Barone . |
| 5,007,414 | 4/1991 | Sexton . |

*Primary Examiner*—Richard J. Apley
*Assistant Examiner*—Linda C. M. Dvorak
*Attorney, Agent, or Firm*—Larson and Taylor

[57] ABSTRACT

A device and method for maintaining and restoring normal curvature of a person's lumbar spine. The device is of non-deformable material, has a base lying in a plane and an upper surface curved in the direction of the sagittal plane to conform to the normal curvature of a person's lumbar spine. The curvature is preferably circular with a radius of between 14 and 20 centimeters, but generally approximately 17 centimeters and the base preferably extends in the direction of the sagittal plane for approximately 17 centimeters. The method of maintaining and restoring the normal curvature of the lumbar spine includes placing the device between a firm surface and the person's lumbar spine and preferably elevating the person's legs 12 to 18 inches for a finite period of time.

12 Claims, 3 Drawing Sheets

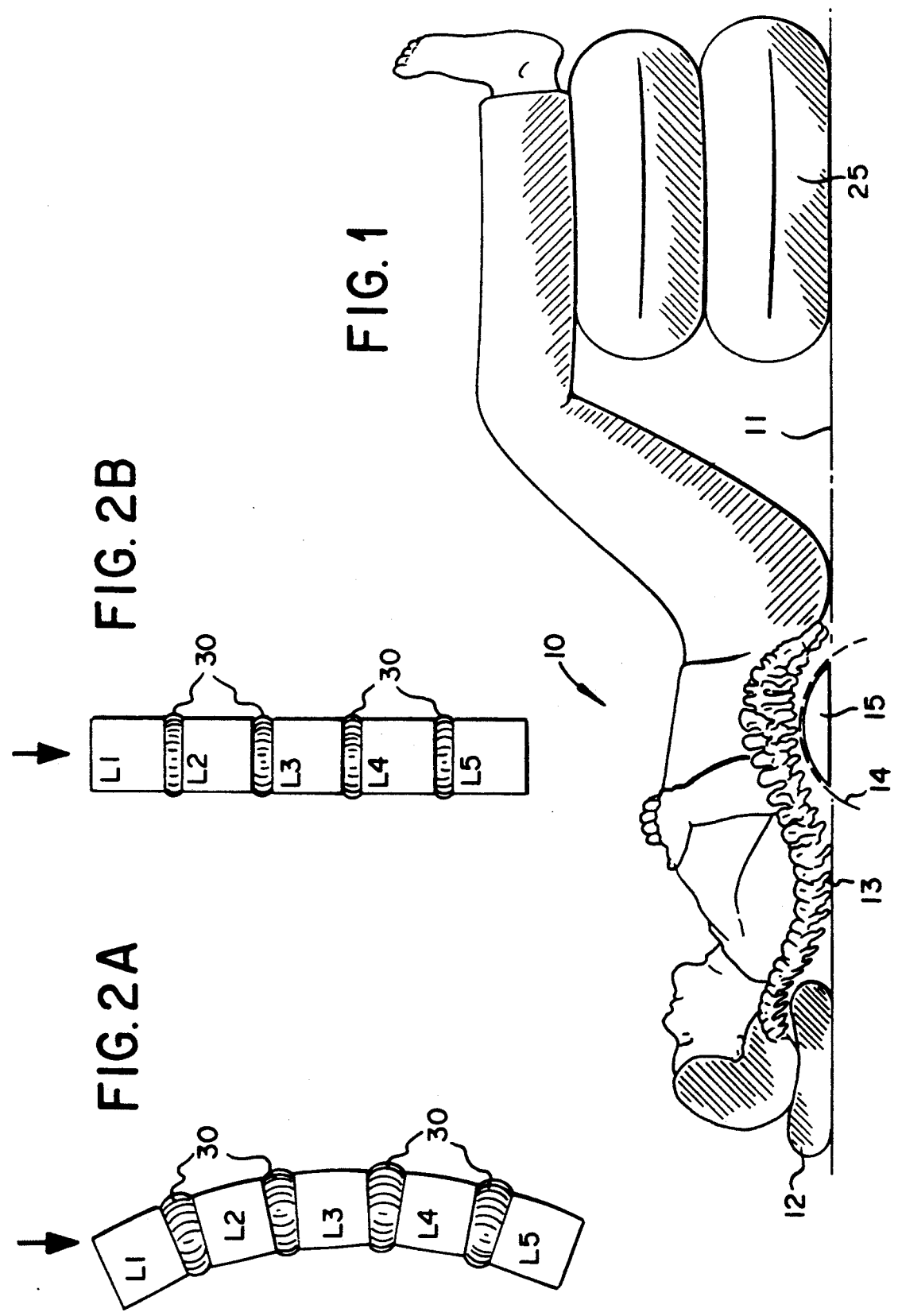

METHOD AND DEVICE FOR MAINTAINING OR RESTORING NORMAL LUMBAR CURVATURE

FIELD OF THE INVENTION

This invention relates to treatment of the human lumbar spine, and in particular it relates to a new and improved method and device for maintaining and restoring normal curvature of a person's lumbar spine.

BACKGROUND OF THE INVENTION

The lumbar spine is placed under great stress on a regular basis through the normal postural activities of sitting, standing and lifting. Studies have shown that as muscles fatigue they tend to shorten, which creates changes in the normal spinal curve. Changes in the spinal structure affect the biomechanical function of the vertebrae, discs and ligaments of the lumbar spine. The loss of proper mechanical function or dysfunction of the lumbar spine increases the formation of spondylosis (degenerative arthritis) with a tendency towards premature disc degeneration, disc herniation and eventually calcification of the involved spinal structures.

It has been known heretofore that these stresses could be relieved by having the person lie on his or her back with a support located in the small of the back. This has been referred to as "spinal remolding" as described in a booklet entitled "Spinal Care", published by Krames Communications. Relieving these stresses is also referred to in the Rogers U.S. Pat. No. 3,359,577.

However, these known arrangements, which are generally of deformable material, have been of limited utility and their beneficial effects have been of limited duration. It is believed that these limitations of the prior arrangements result because they have been structured to provide short term comfort and support, and not long term maintenance and restoration of the lumbar region.

A need therefore exists to utilize the concept of spinal remolding as a therapeutic and preventative tool, thereby resulting in longer term relief than is now possible using the shorter term comfort and support arrangements.

SUMMARY OF THE INVENTION

The purposes of the present invention are to provide a method and device for long term therapeutic rehabilitation of the lumbar spine and prevention of the premature degenerative process.

A healthy lumbar spine has a normal, healthy curvature. Under normal day-to-day conditions, the lumbar spine is subjected to stresses resulting from activities including, for example, exercise, lifting, prolonged sitting, standing or driving, poor posture or wearing high heels. As a result of these stresses, the back muscles contract, resulting in a shortening of the lumbar spine, or more specifically, shortening of the vertebral motor units which consist of adjacent lumbar vertebrae, the disc between them and all attached ligaments and muscle structures. As a result of this shortening, the lumbar spine becomes shortened and relatively straight, as opposed to its healthy more elongated normal curvature. In a healthy person, the subsequent regular periods of muscle relaxation, including sleep or appropriate exercise will allow the lumbar spine to elongate to its normal length and curvature.

However, even in a so-called healthy person, the effects of these daily stresses may not completely reverse themselves during the regular intervals of relaxation. If not, then these effects may become additive, long before the person experiences any pain or discomfort. The term "prevention" refers to actions which assist a person with a healthy back or a person at the early non-pain, non-discomfort stages to continuously restore a normal lumbar spine curvature, thus preventing additive shortening thereof. The term "therapeutic" refers to similar treatment of a person who has started to experience pain or discomfort to restore a normal lumbar spine curvature and relieve pain and discomfort.

The purposes of the present invention are achieved by providing a non-deformable surface placed non-yieldingly against and curved to match the curvature of the normal lumbar spine. With this arrangement, as the muscles relax, the person's own body weight acts, in cooperation with the non-deformable curved surface, as a passive traction, causing the lumbar spinal structures to elongate solely by movement along that curved surface, and not into that curved surface, as would be the case if the surface were deformable. As the lumbar spine, including the lumbar vertebrae, the discs and all attached ligament and muscle structures elongate along this non-deformable surface upon relaxation of stresses, then (1) in the case of a healthy person a normal lumbar spinal curvature is maintained, improving overall spinal health and reducing the chances of back pain or back injury, while (2) in the case of a person already experiencing pain or discomfort, normal mechanical functioning is restored and pain sensitive structures are calmed.

In accordance with a preferred embodiment of the present invention, there is provided a non-deformable device having a base located in a plane and an upper surface above the base which is curved in the person's sagittal plane and of a length in that plane so as to fit into the small of the person's back and up against at least the first to fifth lumbar vertebrae. In addition, in a preferred embodiment, the device will also extend far enough in the direction of the sagittal plane to engage the lowermost thoracic vertebrae and the uppermost sacral vertebrae. The device must be designed to fit each different individual. Since individuals are of different sizes, different sized devices are necessary. Whatever the size, the devices have in common an upper surface having a curvature, preferably a circular curvature, the device extending for a length essentially equal to the small of the person's back, while concurrently permitting the person's body above and below the device to engage the floor. For an average size person, the device would have a radius of curvature of approximately 17 centimeters, a height at its highest point of approximately 2.3 centimeters and a length in the direction of the sagittal plane of approximately 17 centimeters. The upper surface, which is curved in the direction of the sagittal plane, is preferably straight across in the transverse direction, preferably approximately 17 centimeters, while at its ends, taken in the direction of the sagittal plane, the curved surface intersects the base thereof. Accordingly, the device preferably has the form of a section of a right cylinder. For persons of different sizes, the radius of curvature of the upper surface can range from 14 to 20 centimeters. At one extreme, given a radius of curvature of 14 centimeters, the length of the device in the sagittal plane would be approximately 15.31 centimeters and the height of the curvature at its highest point would be approximately 2.3 centimeters. At the other extreme, given a radius of curvature of 20 centimeters, the length of the device in the sagittal plane would be approximately 18.54 centimeters and the height would be approximately 2.3 centimeters.

In a preferred method of the present invention, maintenance or restoration of the normal curvature of the person's lumbar spine is accomplished by having the person lay on his or her back, on a firm surface, with the above described device in the small of the back with its upper surface fitting snugly against the person's lumbar vertebrae plus the lowermost thoracic and the uppermost sacral vertebrae, while elevating the person's legs, with the device in place, for a finite period of time.

Thus, it is an object of the present invention to provide a method and device for therapeutic and preventative treatment of the lumbar spine.

It is another object of the present invention to provide a method and device for maintaining and restoring normal lumbar spine curvature, whereby a non-deformable surface curved to match the normal curve of a person's lumbar spine is brought up against that lumbar spine, with that person lying on his or her back, whereby passive traction caused by the cooperation of the non-deformable curved surface and the person's weight cause lumbar spine to elongate along the curved surface.

It is still another object of the present invention to provide a device of a non-deformable material, of a size which fits snugly within the small of a person's back and having an upper surface which fits snugly against that person's first to fifth lumbar vertebrae plus the lowermost thoracic and the uppermost sacral vertebrae, so as to support same during restoration and maintenance of a normal spinal curve.

It is still another object of the present invention to provide a therapeutic and preventative method, utilizing the device as described above, to maintain and restore normal lumbar spinal curvature.

These and other objects of the present invention will become apparent from the detailed description to follow.

BRIEF DESCRIPTION OF THE DRAWINGS

There follows a detailed description of preferred embodiments of the present invention which are to be taken together with the accompanying drawings, wherein:

FIG. 1 is a side view of a person lying down on a firm surface and utilizing the method and device of the present invention.

FIG. 2A is an enlarged view of the lumbar vertebrae having a normal curvature.

FIG. 2B is an enlarged view of the lumbar vertebrae under increased vertical stress.

DETAILED DESCRIPTION OF THE PREFERRED EMBODIMENTS

Figure 3:
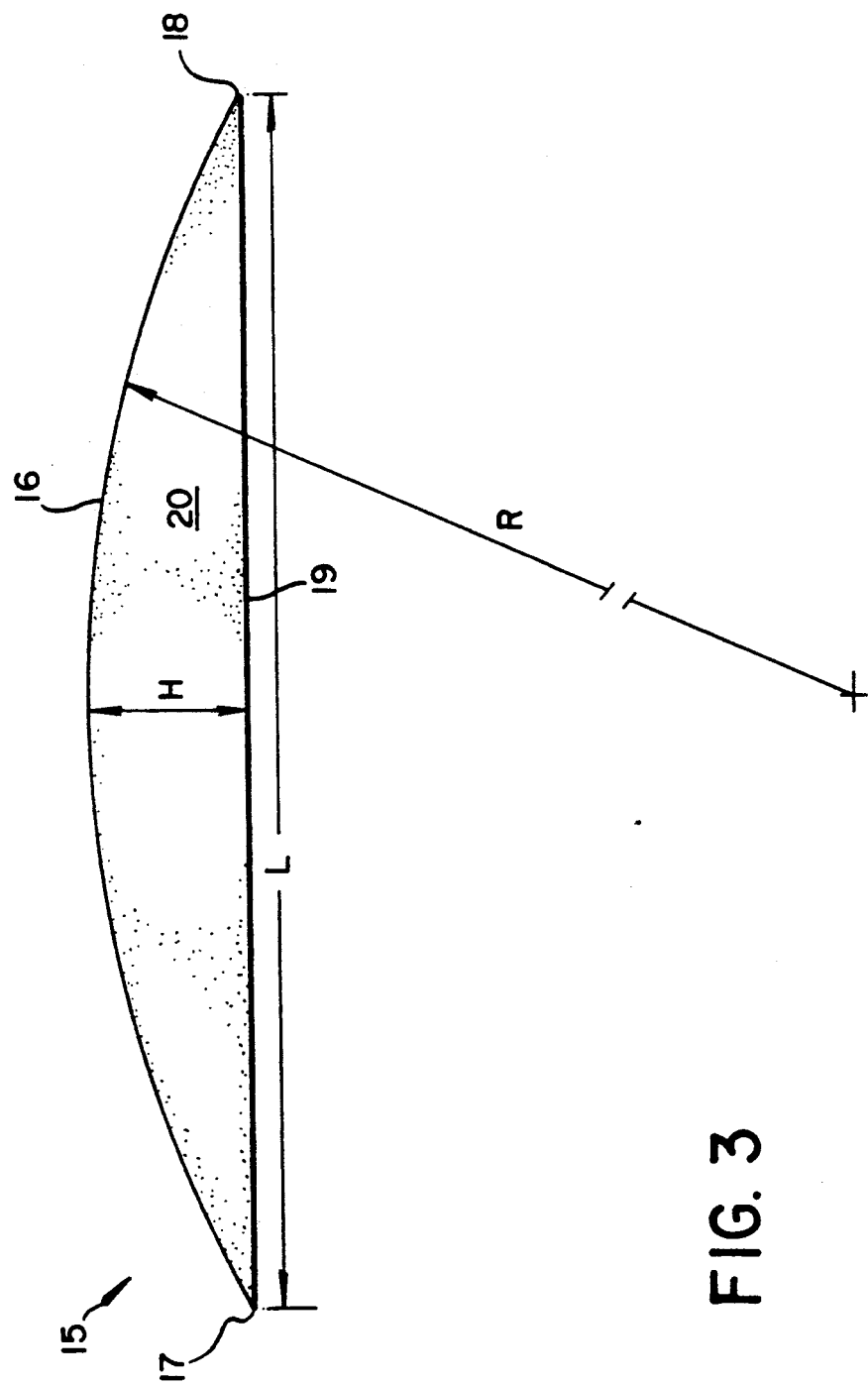
FIG. 3 is a side elevational view of the device of the present invention, showing a preferred embodiment thereof in actual size.

Referring now to the figures, like elements are represented by like numerals throughout the several views.

Referring to FIG. 1, a person 10 being treated in accordance with the present invention is shown lying on a firm surface 11, for example a hard floor surface, with his head resting on a pillow 12. The spine 13 is illustrated, as is the natural curvature 14 of the lumbar spine. The device 15 is positioned between the surface 11 and the lumbar spine such that it does not extend in the direction of the sagittal plane beyond the small of the back and such that its upper surface closely matches the natural lumbar spine curvature 14, as a result of which the upper surface fits snugly and because it is non-deformable, unyieldingly against the person's lumbar spine. The treatment is directed essentially to the lumbar spine, including the first to fifth lumbar vertebrae. However, to provide a snug fit into the small of the back, so as to support the first to fifth lumbar vertebrae, the device actually extends beyond these lumbar vertebrae. For example, referring to FIG. 1, the end of the device 15 closest to the actually positioned beneath the lowermost thoracic vertebrae, i.e., the twelfth and possibly eleventh thoracic vertebrae. At the other end, the device 15 will extend beneath the uppermost sacral vertebrae, i.e., the first and possibly the second sacral vertebrae. In accordance with a preferred method of the present invention, when the device 15 is in place as described above, the person's legs are elevated, for example as shown resting on pillows 25.

FIGS. 2A and 2B are enlarged schematic views of the lumbar spine, shown vertically corresponding to a person standing upright. FIG. 2A illustrates diagrammatically a healthy lumbar spine with a normal curve. The lumbar vertebrae are indicated as L-1 through L-5 with healthy disc material 30 shown between them.

FIG. 2B illustrates the same lumbar vertebrae L-1 to L-5, after increased vertical stress has shortened the vertebral motor units, i.e., adjacent lumbar vertebrae (including the pairing of the fifth lumbar vertebrae and the sacrum), the discs between them and all attached ligaments and muscle structures. Such shortening will have resulted from muscle fatigue, which can be brought about by numerous activities such as exercise, weight lifting, prolonged sitting, prolonged standing, long car trips, wearing high heels, poor posture, insufficient sleep and/or various lifting and bending routines.

Figure 4:
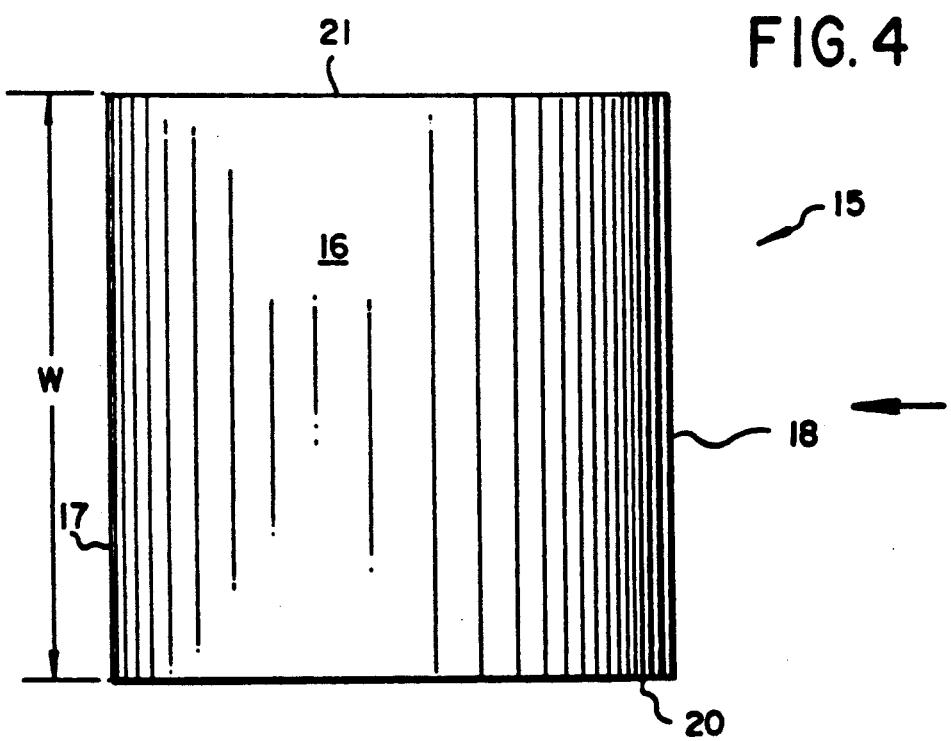
FIG. 4 is a plan view of FIG. 3, on a reduced scale.
Figure 5:
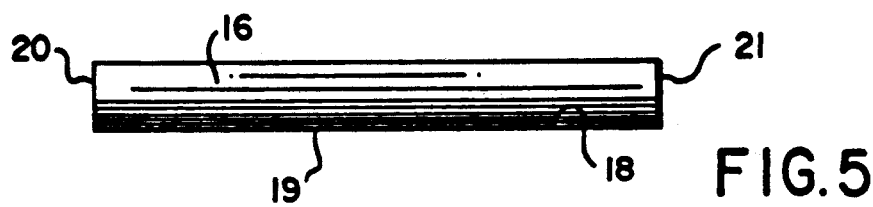
FIG. 5 is a right side elevational view of FIG. 4.

FIGS. 3 through 5 illustrate the device 15 in greater detail. FIG. 3 is an actual size illustration of a device 15 for an average size person, wherein the radius of curvature R is approximately 17 centimeters, the length L is approximately 17 centimeters and the height H is approximately 2.3 centimeters. To be more specific, the height is preferably 2.278 centimeters. FIGS. 4 and 5 show other views, but on a reduced scale. The width of the device, W, as shown in FIG. 4, would preferably also be approximately 17 centimeters. The width W should be sufficient to support the person's back as the person lies on the device 15 and the relaxed spine elongates to its normal curvature.

As shown in FIGS. 3 through 5, the device 15 includes an upper surface 16 having the radius of curvature R which is preferably a circular curvature extending between opposite ends 17 and 18, both of which preferably intersect the base 19 which lies in a plane and in use would rest against the firm surface 11. The device 15 is bounded by side surfaces 20 and 21. The device is generally straight in the direction parallel to the edges 17 and 18 so that the device as a whole is of the shape of a section of a cylinder.

Ideally, the device 15 would be formed of a solid piece of hard material such as wood or injection molded plastic. However, it will be apparent that the device can be hollow so long as the material is sufficiently strong that the upper curved surface 16 does not deform as the person places his or her weight thereon, with at least portions of base 19 resting firmly and solidly against the surface 11.

As noted above, for an average size person, the radius of curvature R would be 17 centimeters, the height H would be approximately 2.3 centimeters, or more specifically 2.278 centimeters when the length L of the base is exactly 17 centimeters. In order to fit different size persons, however, the radius of curvature may vary between 14 and 20 centimeters. For each different radius of curvature, the height H and the length L would be as follows:

| Radius of Curvature (R) in Centimeters | Height (H) in Centimeters | Length (L) in Centimeters |
| --- | --- | --- |
| 14 cm | 2.278 cm | 15.31 |
| 15 cm | 2.278 cm | 15.89 |
| 16 cm | 2.278 cm | 16.46 |
| 17 cm | 2.278 cm | 17.0 |
| 18 cm | 2.278 cm | 17.53 |
| 19 cm | 2.278 cm | 18.04 |
| 20 cm | 2.278 cm | 18.54 |

Figure 6:
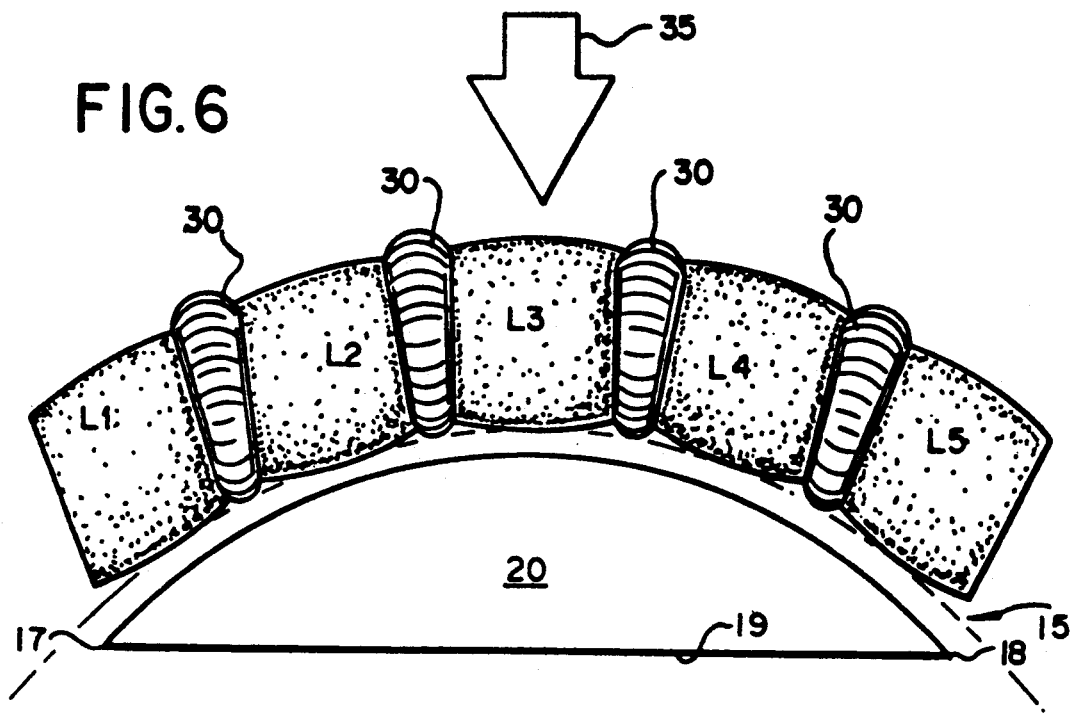
FIG. 6 is a side elevational view in the same direction as FIGS. 1 and 3, but showing the device of the present invention in combination with the lumbar vertebrae resting thereon.

FIG. 6 illustrates the device 15 in conjunction with the lumbar spine with adjacent thoracic and sacral vertebrae omitted for purposes of illustration. As shown therein the main portion of curved upper surface 16 fits snugly against the lumbar vertebrae L-1 through L-5. In FIG. 6 a space is shown between the upper surface 16 and the vertebrae to represent the space which would normally be taken up by the spinal process. Assuming that these vertebrae were originally under stress, for example as shown in FIG. 2B, the gravitational force of the person's weight, as indicated by arrow 35 exerts a passive traction force causing the lumbar spine to elongate in the direction of the sagittal plane down the slopes of curvature 16. The non-deformability of the surface 16 is essential in that it forces the lumbar vertebrae to move in their direction of elongation of the spine, thereby restoring and maintaining the normal spine curvature with increased efficiency.

In accordance with a preferred method of the present invention, a person is placed as shown in FIG. 1, wherein the lumbar spine is supported as best shown in FIG. 6. The legs are elevated 12 to 18 inches off of the firm surface 11, for example using pillows 25 or the like. Preferably, this is done in 20 minute sessions, one to two times per day.

Although the invention has been described in considerable detail with respect to preferred embodiments thereof, variations and modifications will be apparent to those skilled in the art, without departing from the spirit and scope of the invention, as set forth in the claims.

I claim:

1. A device for maintaining or restoring normal curvature of a person's lumbar spine comprising:

a structure consisting essentially of a base lying in a base plane for cooperating with a flat support surface, an upper surface having a curvature in a first direction which corresponds essentially to the normal curvature of a person's spine and extending in said first direction a sufficient distance to support the person's first through fifth lumbar vertebrae, and still allowing the ilia and substantially the entire sacrum to rest on the flat support surface, and extending across in a second direction perpendicular to the first direction essentially straight and continuous and far enough to support the person's back muscles on each side of the vertebrae sufficiently to allow the first through fifth lumbar vertebrae to conform to said curvature in the first direction, said upper surface curvature being circular so as to form a section of a cylinder, the upper surface being non-deformable from end to end so as to essentially maintain its shape as the person's weight is placed upon its, the circular curvature having a radius of curvature between 14 and 20 centimeters and the height of the device from the base plane to the highest point being between 2 to 2.5 centimeters, whereby, when a person lies on the device with the device placed in the small of the person's back, the person's weight, being resisted vertically by the non-deformability of the device, is distributed along the curved upper surface of the device to promote passive traction of the lumbar spine.

2. A device according to claim 1, wherein radius of curvature is approximately 17 centimeters and the said height is approximately 2.3 centimeters.

3. A device according to claim 2, the upper surface extending essentially straight for approximately 17 centimeters in the second direction.

4. A device according to claim 1, the curved upper surface engaging the base plane at both ends thereof, the radius of curvature being approximately 17 centimeters and height being approximately 2.3 centimeters.

5. A device according to claim 4, the base extending for approximately 17 centimeters in the second direction.

6. A device according to claim 1, said device being made of wood.

7. A device according to claim 1, said device being made of injection molded polystyrene.

8. A device according to claim 1, wherein the circular curvature of the upper surface engages the base plane at both ends thereof.

9. A method of maintaining or restoring normal curvature of a person's lumbar spine, comprising the steps of:

having a person lie on his or her back on a firm surface with a non-deformable device located between the firm surface and the person's lumbar spine, which device has a base lying in a base plane corresponding to the firm surface, an upper surface having a circular curvature in the head to toe direction, which curvature has a radius of curvature between 14 and 20 centimeters which essentially corresponds to the normal curvature of the lumbar spine, so as to support the person's first through fifth lumbar vertebrae, and still allowing the ilia and substantially the entire sacrum to rest on the flat support surface, and the device being essentially straight and continuous, taken transversely to the head to the toe direction to support the person's back muscles on each side of the vertebrae, elevating the person's legs with the device in place for a finite period of time of between five and twenty minutes, and effecting passive traction, while the device is in place and the legs are raised, by distributing the person's weight, which is resisted vertically by the non-deformability of the device, along the curved upper surface of the device.

10. A method according to claim 9, wherein the radius of curvature is approximately 17 centimeters and the base is also approximately 17 centimeters in the head to toes direction.

11. A method according to claim 9, wherein the person's legs are elevated to approximately 12 to 18 inches.

12. A method according to claim 11, wherein the step of elevating the person's legs is maintained for approximately 20 minutes at a time.

* * * * *